(12) United States Patent
Hummer et al.

(10) Patent No.: US 11,140,880 B2
(45) Date of Patent: Oct. 12, 2021

(54) BEEHIVE STATUS SENSOR AND METHOD FOR TRACKING PESTICIDE USE IN AGRICULTURE PRODUCTION

(71) Applicants: Gregory J. Hummer, Shaker Heights, OH (US); Matthew Hummer, Washington, DC (US)

(72) Inventors: Gregory J. Hummer, Shaker Heights, OH (US); Matthew Hummer, Washington, DC (US)

( * ) Notice: Subject to any disclaimer, the term of this patent is extended or adjusted under 35 U.S.C. 154(b) by 0 days.

(21) Appl. No.: 16/547,737

(22) Filed: Aug. 22, 2019

(65) Prior Publication Data
US 2019/0373862 A1    Dec. 12, 2019

Related U.S. Application Data

(63) Continuation of application No. 15/951,500, filed on Apr. 12, 2018, now Pat. No. 10,555,505, which is a
(Continued)

(51) Int. Cl.
*G08B 21/02*    (2006.01)
*A01K 51/00*    (2006.01)
(Continued)

(52) U.S. Cl.
CPC .............. *A01K 51/00* (2013.01); *A01K 47/06* (2013.01); *G01N 33/0036* (2013.01); *G01N 33/0063* (2013.01); *G08B 21/182* (2013.01)

(58) Field of Classification Search
CPC ........ A01K 47/06; A01K 51/00; A01K 47/00; A01K 49/00; A01K 67/033;
(Continued)

(56) References Cited

U.S. PATENT DOCUMENTS

| 5,238,681 A | * | 8/1993 | Chang | A01N 25/006 |
| | | | | 424/405 |
| 5,933,563 A | * | 8/1999 | Schaffer | G02B 6/4452 |
| | | | | 174/58 |

(Continued)

OTHER PUBLICATIONS

Article Application of Nanotechnology in Pesticides Removal from Aqueous Solutions—A review, T. Taghizade Firozjaee et al., Int. J. Nanosci. Nanotechnol., vol. 14, No. 1, Mar. 2018, pp. 43-56.

*Primary Examiner* — Daniel Previl
(74) *Attorney, Agent, or Firm* — Fay Sharpe LLP

(57) ABSTRACT

Monitoring system, device and method for detecting chemicals in an insect environment, such as a beehive or colony. The method can include monitoring the insect environment for the presence or absence of at least one chemical or environmental factor using at least one sensor located within the insect environment, the at least one sensor operative to generate data in response to the presence or absence of at least one chemical or factor in the environment and communicate the data to an associated data processing device, monitoring a population of insects in the insect environment to detect a change in the population or health of insects that make up the population, and generating a correlation between a detected change in the population or health of insects in the insect environment with an increase or decrease of the at least one chemical outside the insect environment.

17 Claims, 4 Drawing Sheets

Related U.S. Application Data continuation-in-part of application No. 15/891,410, filed on Feb. 8, 2018, now Pat. No. 10,395,503, which is a continuation of application No. 15/235,981, filed on Aug. 12, 2016, now Pat. No. 9,922,525.

(60) Provisional application No. 62/485,084, filed on Apr. 13, 2017, provisional application No. 62/297,385, filed on Feb. 19, 2016, provisional application No. 62/205,012, filed on Aug. 14, 2015.

(51) Int. Cl.
*G01N 33/00* (2006.01)
*G08B 21/18* (2006.01)
*A01K 47/06* (2006.01)

(58) Field of Classification Search
CPC ........... G01N 33/0036; G01N 33/0063; G01N 15/1209; G01N 2015/0038; G01N 33/48721; G01N 29/04; G01N 33/007; G01N 21/1702; G01N 2291/0289; G01N 29/075; G01N 29/11; G01N 29/348; G01N 27/414; G01N 27/122; G01N 27/124; G01N 33/0006; G01N 33/0027; G01N 33/0031; G01N 33/0073; G01N 33/5438; G01N 27/4145; G01N 27/4146; G01N 27/4175; G01N 27/624; G01N 29/222; G01N 29/32; G01N 33/0009; G01N 33/0062; G01N 33/48707; G01N 33/4972; G08B 21/182; G08B 21/12; G08B 25/10; A01G 13/10; A01G 29/00; A01G 31/02; A01G 7/02; A01G 7/06; A01G 9/20; A01G 9/246; E04H 12/20; C12Q 1/6869; C12Q 2563/131; C12Q 2565/631; C12Q 1/689; C12Q 1/6895; C12Q 2600/158; B82Y 30/00; B82Y 15/00; H04L 67/12; H04W 4/38; H04W 52/0206; H04W 84/18; Y02D 30/70; Y02D 70/1224; Y02D 70/1242; Y02D 70/1244; Y02D 70/1246; Y02D 70/1262; Y02D 70/142; Y02D 70/144; Y02D 70/146; Y02D 70/162; Y02D 70/164; Y02D 70/166; Y02D 70/21; C07K 14/705; G05B 15/02; A01M 1/02; A01M 1/2038; A01M 1/2044; A01M 1/205; A01M 1/2077; A61L 9/14; G06K 19/0717; G06K 19/0723; G10H 1/0025; G10H 2220/351; H04B 1/3888; H04M 1/21; H04M 1/7253; H04M 2250/04; H04M 2250/12; Y02A 40/25; Y02P 60/21
USPC ................ 340/539.11, 539.1, 539.26, 691.6, 340/539.27–539.29, 539.32, 555, 683, 340/7.54, 825.49, 825.72
See application file for complete search history.

(56) References Cited

U.S. PATENT DOCUMENTS

| | | | |
|---|---|---|---|
| 6,190,913 B1* | 2/2001 | Singh | B01F 11/0017 435/383 |
| 7,176,793 B1 | 2/2007 | Hummer | |
| 7,667,593 B1 | 2/2010 | Hummer | |
| 7,911,336 B1 | 3/2011 | Hummer | |
| D641,013 S | 7/2011 | Richardson et al. | |
| 8,204,561 B2 | 6/2012 | Mongan et al. | |
| 8,629,770 B2 | 1/2014 | Hummer et al. | |
| 8,674,827 B2 | 3/2014 | Hummer | |
| 8,930,341 B2 | 1/2015 | Amin et al. | |
| 9,241,054 B1 | 1/2016 | Roberts | |
| 9,400,269 B2 | 7/2016 | Kambhampati | |
| 9,466,057 B2 | 10/2016 | Beeson | |
| 9,635,840 B2* | 5/2017 | Reckhaus | A01K 67/033 |
| 9,922,525 B2* | 3/2018 | Hummer | H04M 1/7253 |
| 10,555,505 B2* | 2/2020 | Hummer | G01N 33/0063 |
| 2004/0119591 A1 | 6/2004 | Peeters | |
| 2006/0049714 A1 | 3/2006 | Liu | |
| 2007/0218804 A1* | 9/2007 | Allan | A01K 49/00 449/4 |
| 2010/0236383 A1* | 9/2010 | Vogel | G10H 1/0025 84/600 |
| 2011/0263182 A1* | 10/2011 | Custer | A01K 47/06 449/15 |
| 2013/0271286 A1 | 10/2013 | Quan | |
| 2014/0162711 A1* | 6/2014 | Miller, II | H04W 84/18 455/500 |
| 2014/0349707 A1 | 11/2014 | Bang | |
| 2014/0370781 A1* | 12/2014 | Anderson | A01K 47/02 449/5 |
| 2014/0377130 A1 | 12/2014 | Edwards | |
| 2015/0180525 A1 | 6/2015 | Chen | |
| 2015/0310720 A1* | 10/2015 | Gettings | G08B 29/188 340/540 |
| 2015/0326061 A1 | 11/2015 | Davison | |
| 2015/0359208 A1* | 12/2015 | Reckhaus | G01N 33/5085 119/6.5 |
| 2017/0360010 A1* | 12/2017 | Wilson-Rich | A01K 51/00 |
| 2018/0038815 A1 | 2/2018 | Gu et al. | |
| 2018/0103206 A1 | 4/2018 | Olson | |

* cited by examiner

BEEHIVE STATUS SENSOR AND METHOD FOR TRACKING PESTICIDE USE IN AGRICULTURE PRODUCTION

CROSS REFERENCE TO RELATED PATENTS AND APPLICATIONS

The present application is a continuation of U.S. patent application Ser. No. 15/951,500, filed Apr. 12, 2018, which application claims the benefit of U.S. Provisional Patent Application No. 62/485,084, filed on Apr. 13, 2017, and is a continuation-in-part of U.S. patent application Ser. No. 15/891,410, filed on Feb. 8, 2018, which is a continuation of U.S. patent application Ser. No. 15/235,981, filed Aug. 12, 2016, now U.S. Pat. No. 9,922,525, issued Mar. 20, 2018, which claims the benefit of U.S. Provisional Patent Application Ser. No. 62/297,385, filed Feb. 19, 2016 and U.S. Provisional Patent Application Ser. No. 62/205,012, filed Aug. 14, 2015, which applications are hereby incorporated by reference.

FIELD

The present exemplary embodiment relates to systems and methods for detecting chemicals or environmental factors. It finds particular application in conjunction with systems and method for detecting chemicals or factors in a beehive or other social insect colonies as well as in the environments in which they interact and will be described with particular reference thereto. However, it is to be appreciated that the present exemplary embodiment is also amenable to other like applications.

BACKGROUND

Pollinators are critical to the Nation's economy, food security, environment and health. Honey bee pollination alone adds more than $15 billion in value to agriculture crops each year. It also helps to improve public health by ensuring the availability of ample fruits, nuts and vegetables, which are part of a balanced diet. In addition, honey bee pollination enhances land conservation, which makes ecosystems more resistant to climate change and natural disasters.

But pollinators are struggling, particularly honey bees. In 2016, reported losses of all managed colonies in the U.S., amounted to 44.1 percent. The annual losses increased 3.5 percent from the previous year—the first year in which summer season losses exceeded winter season losses. As a result of the high rate of loss, beekeepers are working harder to replace and/or maintain their colonies.

The economic impact of bee colony loss is significant. The estimated direct cost to beekeepers alone totals $2 billion. The estimate assumes that 10 million hives have been lost at a conservative valuation of $200 each. Looking at just this past year, the estimated direct cost to beekeepers is almost $500 million. Another estimation approach based on lost agriculture output puts the economic burden much higher at more than $4.4 billion.

High colony loss rates require beekeepers to rapidly, and at substantial expense, rebuild their colonies, placing commercial beekeeping in jeopardy as a viable industry and threatening the crops dependent on honeybee pollination.

Despite challenging circumstances, commercial beekeepers have been somewhat successful at passing along the added costs of colony loss. For example, the cost of renting honey bees for almond growers rose from $51.99 per colony in 2003 to as much as $157.03 per colony in 2009.

In recent years, research has focused on the causes of colony loss or Colony Collapse Disorder (CCD), a phenomenon that occurs when worker bees leave an otherwise healthy colony. Research suggests that the declining bee population could be caused by the "combined stresses" of parasites, pesticides and habitat loss. However, now that some of the causes are known, finding ways to help minimize loss and achieve goals set forth in the National Strategy to Promote the Health of Honey Bees and Other Pollinators is critical. The strategy calls for reducing overwintering mortality to 15 percent within ten years. However, recent data show that winter loss rates are on the rise and well above the acceptable level. Overwintering motility increased 5.8 percentage points to 28.1 percent this past winter from 22.3 percent in the previous winter.

FIG. 1 illustrates that overwintering mortality, a key metric for determining the overall health of honey bees, is on the rise. The share of colonies lost during the 2015-2016 winter was 28.1 percent, which significantly exceeds the sustainable level of 15 percent of commercially managed colonies in the U.S.

Current approaches to increase overall colony health have focused primarily on monitoring chemical composition using sampling techniques and gas chromatography. However, the method provides only a snapshot of chemical composition and does not monitor in real-time the changes to chemical composition and how those changes affect the overall health of honey bee colonies. Less scientific methods are also being deployed. Many commercial beekeepers have accepted high colony loss rates of about a quarter of their bees on average and are having to rebuild their hives from scratch. The rebuilding process typically takes about two months and involves transferring bees from a healthy colony to a new hive. These bees produce a hatch of baby bees and food to support them. A queen bee is required, and one queen now costs upwards of $25. It is not unusual for commercial beekeepers to spend hundreds of thousands of dollars per year just on queen bees.

Current methods fall short of preventing honey bee loss and instead focus on coping with the fallout hive collapse.

SUMMARY

The present disclosure provides necessary data to commercial farmers and commercial beekeepers to allow them to determine the appropriate level of pesticide use that protects plants from pests, but also prevents harm to sources of natural pollination, including honey bees.

Two critical honey bee pheromones, 9-ODA and E-β-ocimene, have a significant impact on the health of honey bee colonies. Specifically, 9-ODA (EC50=280±31 nM), is the only queen retinue pheromone (QRP) that also acts as a long-distance sex pheromone. For the first time, and in accordance with the present disclosure, continuous monitoring of the target pheromones and levels at which they exist in colonies will be possible. Other chemicals can be monitored in addition or in the alternative, as appropriate, including various forms of pesticides including: dichlorodiphenyltrichloroethane (DDT), organophosphates such as malathion and diazinon and neonicotinoids among other insecticides. It should be appreciated that any factor that impacts crop production and has an impact on pollinators that interact with such crops can be monitored so that remedial action can be taken.

In accordance with one aspect, a method of monitoring the health of an insect environment comprises monitoring the insect environment for the presence of at least one chemical using at least one sensor located within the insect environment, the at least one sensor operative to generate data in response to the presence of at least one chemical in the environment and communicate the data to an associated data processing device, monitoring a population of insects in the insect environment to detect a change in the population, and generating a correlation between a detected change in the population of insects in the insect environment with an increase or decrease of the at least one chemical. In some cases, insect detected and used instead of population. For example, an acceptable population of bees could be present in the hive, but not doing their job brooding, cleaning and foraging. This will ultimately result in fewer bees as they die off from lack of food.

The method can include monitoring one or more environments external to the insect environment with which the insect population interacts for the at least one chemical, and taking remedial action to increase or decrease the at least one chemical in the insect environment based at least in part on the correlation between a detected change in the population of insects in the insect environment with an increase or decrease of the at least one chemical. The remedial action can include increasing or decreasing a concentration of the at least one chemical in the one or more environments external to the insect environment. The method can include monitoring at least one of temperature or humidity of the insect environment. The insect environment can include a beehive. The at least one sensor can be configured to periodically report a sensed concentration of the at least one chemical to the associated data processing device over a period of time.

The method can further include comparing the sensed concentration to a threshold concentration, and generating an alert if the sensed concentration exceeds the threshold concentration. The method can include providing a power source including an antenna configured to receive energy wirelessly and supply the received energy to at least one of the detector component or the communication circuitry.

In accordance with another aspect, a monitoring system for monitoring an environment for the presence of one or more chemicals comprises a receiver, a first sensor including a detector component operative to generate data in response to the presence of one or more chemicals, communication circuitry and a power source operatively coupled to the detector component and the communication circuitry for supplying power thereto, the communication circuitry configured to transmit data generated by the detector component corresponding to the presence or absence of one or more chemicals to the associated receiver, and a second sensor including a detector component operative to generate data in response to the presence of one or more chemicals, communication circuitry and a power source operatively coupled to the detector component and the communication circuitry for supplying power thereto, the communication circuitry configured to transmit data generated by the detector component corresponding to the presence or absence of one or more chemicals to the receiver. The first sensor is configured to detect one or more chemicals in an insect environment, and the second sensor is configured to detect one or more chemicals in an environment external to the insect environment with which the insect population interacts.

The monitoring system can include various forms of sensor apparatus including an apparatus placed directly inside of the colony and or an apparatus connected to the colony and continuously samples and detects chemical composition changes in the colony. The sensors placed inside the colony are placed in a protective covering made of substance that allows for optimal performance of the sensor, such as mesh, foam or other material. The system can further include at least one sensor for detecting at least one of a level of insect activity within the insect environment or a population of insects within the insect environment, wherein the receiver is operatively connected with a data processing device configured to generate a correlation between a detected change in the population of insects in the insect environment with an increase or decrease of the at least one chemical. The at least one sensor for detecting at least one of a level of insect activity sensor can be at least one of a temperature sensor, humidity sensor, acoustical sensor, a vibration sensor, and infrared sensor or an ultrasonic sensor. The data processing device can be configured to generate an alert in response to a detected change in population of the insect environment, and/or to generate an alert in response to detection of a predetermined chemical in the insect environment. The power source of at least one of the first or second sensors can include an antenna configured to receive energy wirelessly and supply the received energy to at least one of the detector component or the communication circuitry.

DETAILED DESCRIPTION

Figure 1:
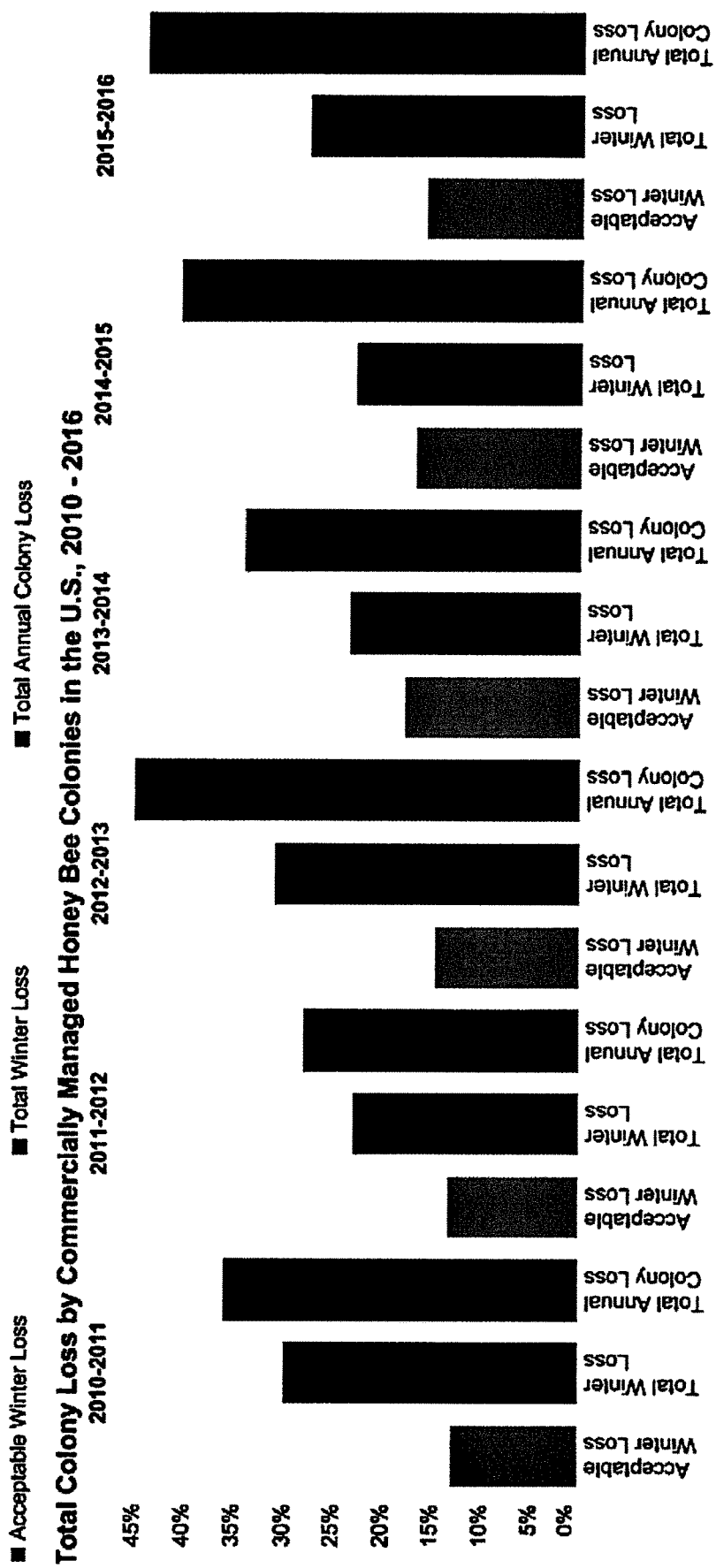
FIG. 1 is a table depicting total bee colony loss over the period 2010-2016.

The present disclosure sets forth a monitoring system for bee colonies and the environments in which they interact including: ant farms, termite mounds, mosquito nests and other organizations of social insects including, but not limited to: bees, wasps, hornets, ants, termites, mosquitos, earwig, stonefly, crickets, dragonfly, fleas, thrips, beetles, stink bugs and butterflies. The present disclosure is focused on social insects, particularly those that interact with agriculture and other types of crops that have monetary value. Honey bees are especially important because they serve a vital role in pollinating a very large portion of the global food supply. Aspects of the present disclosure can be used to monitor any desired insect colony. In a basic example, the system can include sensor and/or other detection devices housed within or in proximity to a hive or nest, a power source and circuitry to communicate data generated by the sensor and/or other detection devices wirelessly with handheld devices and data terminals.

The monitoring system can be calibrated using a method that determines how social insect pheromones respond to various conditions and chemicals, particularly those used in seeds or to treat plants with objective of increasing agriculture production yield. The method can include using any type of carbon particle, nanoparticle, nanoscrolls, nanowire, graphene, microelectrochemical system (MEMS), polymers, gas chromatography, gas chromatography and/or mass spectrometry (GC/MS), miniaturized GS/MS or GS, pulsed discharge ionization detector (PDID) or other sensing device in combination with preconcentrators (PC), including micro-PC and Solid-Phase Microextraction (SPME) to determine the chemical composition of a healthy colony versus an unhealthy colony. The method determines causality between certain conditions and chemicals that contribute to a healthy colony becoming unhealthy and ultimately leading to the collapse of the colony otherwise known as Colony Collapse Disorder (CCD) or any other known or unknown cause of social insect loss. Once the conditions and chemicals that have adverse effects are identified, smaller, more cost-effective nano/meso/micro sensors are developed to monitor the levels of adverse chemicals and conditions inside the colony.

The smaller, more cost-effective sensors of the present disclosure are intended to detect levels of chemicals that are known to have effects on colony health including, but not limited to: pheromones, pesticides, various forms of insecticides and any other chemical composition that may be present in the organization of social insects. With an understanding of the level of target chemical composition, the operating status and health of a social insect organization can be deduced using algorithms, machine learning and artificial intelligence and tracked and traced using blockchain.

The detection device (e.g., sensor component) can comprise an array of sensors and other detection devices (e.g., as noted above) that are connected to an analyzer and memory which contain algorithms, which can be downloaded from a central source, that allow the sensors and other detection devices to differentiate multiple chemicals, gases and environmental conditions including temperature and humidity. By placing the sensors in colonies of social insects, primarily honey bees, and throughout the environment that they interact with (e.g., crop fields and the broader nature ecosystem), the system can identify levels of target chemicals and track where such target chemicals came from outside of the colony. The sensors communicate with the CPU/memory and then report their findings via a standard wireless connection, near-field or other forms of wireless connection which can be encrypted. The sensor(s) are placed inside a protective pouch (made of mesh or any other type of fabric that is permeable, yet protects the sensor allowing it to functional optimally) and attached to the Queen Excluder located at the center of the colony. The sensor can also be strategically placed in other locations of the colony including: the honey supers, out cover, inner cover, deep super, bottom board as well as other areas. Placement in the Queen Excluder is optimal for detecting changes in hive chemical composition and pheromones, especially during the winter months where most brooding occurs. As will be appreciated, sensor placement can be tailored such that it is in suitable location for sensing the target chemical. The design and placement accounts for the harsh environment of social colonies, particularly honey beehives, which maintain temperatures between 81 and 93 degrees Fahrenheit. Also included in the colony chemical monitoring device are humidity and temperature sensors.

The present disclosure sets forth various detection devices placed inside or attached to the outside an organization of social insects, including, but not limited to: bee colonies, ant farms, termite mounds and mosquito nests that collect, detect analyze and communicate levels of target chemicals within the organization that are helpful in determining behavior and overall health of the social insect organization. Significantly, the present disclosure further utilizes similar detection devices deployed in agriculture fields and its surrounding environment to help determine the source of the chemicals that are having harmful affects on honey bee colony health, such that remedial measures can be initiated proactively to avoid damage to the insect population.

Aspects of the present disclosure provide researchers and keepers of social insects up-to-date, real-time information on the status of insect organization health, population or other factors providing indication of the ability to sustain insect organization and their behaviors such as pollination in the case of honey bees.

The present disclosure also sets forth a method and system of placing sensors throughout the environments for which the social insects interact including sources of food, nutrients and water such as nearby irrigation infrastructure, streams, rivers ponds and lakes. The detection devices can also be placed throughout agriculture fields including in soil, on farming equipment, irrigation infrastructure, plants and in stationary and mobile units (including drones and other unmanned/remote/autonomous vehicles specifically for detecting levels of chemicals and other environmental conditions including temperature, humidity and other factors that affect agriculture production.

In accordance with the present disclosure, continuous monitoring of the target pheromones and levels at which they exist in colonies will be possible. Using a staged development approach, bench scale analytical chemistry and statistical analysis is first used to identify target pheromones and chemicals for monitoring. The results are used to inform the development of the hive-side portable system for real-time monitoring and analysis of the target pheromones, as well as other chemicals like pesticides and volatile organic compounds (VOCs). After the hive-side device identifies the chemicals that are known to have a causal effect on colony health, smaller more cost-effective sensors are then configured and placed where monitoring is desired. These locations will relate to where the social insects travel to or reside, primarily inside of their colonies and the agriculture fields or other environments that they come into contract with.

These devices (the hive-side monitoring device and cost-effective nano-sensors) provide researchers and beekeepers with a better understanding of how changes in chemical composition and other environmental factors affect the health of colonies. Once the optimal chemical compositions of healthy colonies are determined, steps can be taken to maintain such compositions and prevent colony loss. Such an approach and system delivers large benefits to beekeepers, especially commercial keepers who struggle to keep an adequate level of healthy honey bee colonies used for pollinating commercial agriculture fields and farms.

The hive-side monitoring system analyzes the volatile signatures from healthy and collapsing colonies using gas chromatography and mass spectrometry (GC/MS) as well as other sampling and measurement techniques including but not limited to: miniaturized Gas Chromatography (GC) utilizing nanoelectrochemical sensors (NEMS) and gas chromatograph-mass spectrometer on chip; miniaturized GC column using MEMS fabricated on a 2 cm×2 cm size µ-GC chip and coated with non-polar stationary phase, was 1.3 m long, 150 µm wide, and 400 µm deep and contain embedded micro circular posts which are 30 µm diameter. Another approach using a 1.5×3 cm microfluidic platform with a sample injection unit, a micromachined semi-packed separation column (µSC) and a micro-helium discharge photoionization detector (μDPID). The sample injection unit consists of a T-shaped channel operated with an equally simple setup involving a single three-way fluidic valve, a micropump for sample loading and a carrier gas supply for subsequent analysis of the VOCs. The hive-side system also leverages advanced algorithms to determine diagnostic patterns indicative of both types of colonies. However, before analyzing a complex volatile mixture using data algorithms, the chemical compounds are separated by gas chromatography and other techniques.

The present disclosure overcomes significant pheromone sampling, separation and detection challenges existing today. For example, pheromones can have strong effects even at very low concentrations, so methods to measure them must be very sensitive. However, most methods and equipment currently being used by researchers require that samples be collected in laboratories, which is difficult to do; is time consuming and tends to bias results. Having portable field detector devices that can sample, separate and detect low concentrations of chemical compounds fundamentally changes the way bee researchers and bee keepers monitor pheromone production over time. Furthermore, the present disclosure helps advance the understanding of how the changing chemical composition of colonies affect overall colony health.

Colonies of social insects are often harsh environments conducive to the survival of a particular species. For example, honey bees precisely control the temperature inside their hives to determine which job their young will perform in the colony when mature. With such precision in their operating environment it is critical that the internal sensors not disrupt activity within the hive, as this could be detrimental in itself to hive health.

For beekeepers, it is very difficult to track hive health during winter because when the colony is hibernating it is inadvisable to open the hive. During the winter, when the temperature drops below 50 degrees Fahrenheit, honey bees retreat into their hive in order to conserve heat and protect the queen bee. They form a cluster in the middle of the hive surrounded the queen, constantly fluttering their wings so the core of the cluster is only able to move vertically within 81-93 degrees. Due to the vertical slat construction of the hives, the cluster is only able to move vertically within the hive, constricting the amount of honey they can consume. In order to reach the honey in the corners of the hive, the bees must break the cluster, a process in which bees lose significant amount of heat. In a best case scenario, by the time the bees need to break cluster the weather will be warm enough for the bees to survive. However, this is not always the case. The sensor system of the present disclosure can monitor not only the temperature and humidity within the hive, but also the exact chemical composition of the hive and how it changes over time correlating with the overall health of a hive.

Because of the challenges described in the previous section, the present disclosure sets forth miniaturized nanotube sensors calibrated to detect changes in the levels of target chemicals produced using metallic ink, screen printing or laser printing. The sensor device can consist of a nano sensor or array of nano sensors that are connected to an analyzer CPU and memory that contains algorithms, which can be downloaded from a central source that allow the sensors to differentiate multiple chemicals, gases and other environmental conditions including temperature and humidity. The sensors communicate with the CPU/memory and then report their findings via standard wireless connection, near-field or other wireless connection which can be encrypted if desired.

The technical challenges overcome by the present disclosure measure levels of critical pheromones, such as 9-ODA and E-β-ocimene, and distinguish between colonies that are strengthening in health versus deteriorating and the conditions causing the change in health. If a colony is identified as deteriorating, steps can be taken such as: replacing old comb with new foundation, providing adequate ventilation, keeping mite infestations in check and treating colonies with an antibiotic to prevent foulbrood, among other factors that contribute to hive deterioration.

A pheromone detection system that provides early warning to colony loss has the ability to contribute significantly to the National Strategy to Promote the Health of Honey Bees and Other Pollinators overwintering mortality goal of 15 percent within ten years. If the system can help return colony loss rates to sustainable levels, or avoid losing one million colonies a year, it would yield at least $200 million a year in direct economic benefit to beekeepers alone.

The non-invasive pheromone detection system and method of the present disclosure offers a number of distinct advantages for bee researchers and beekeepers:

researchers are able to continually detect whether a pheromone is present in a hive, and also continually detect how pheromone levels change in a colony over time. They can also use time-series analysis to correlate those changes to the overall chemical composition of a colony and ultimate hive health and sustainability. This level of functionality will help researchers produce conclusive evidence on how certain chemicals affect colony health.

beyond just pheromones, the detection system can identify as many as 50 target compounds within seconds, helping to identify other compounds, chemicals and environmental factors that have a causal link to the all-important 9-ODA, E-β-ocimene as well as other pheromones and chemicals including, but not limited to pesticides, insecticides and other environmental factors.

aspect of the present disclosure set forth a portable, sensitive and ruggedized system for field use. It also has the ability to communicate wirelessly with remote data terminals or hand-held devices that integrate with sensors deployed in agriculture fields and their surrounding environments, including nature ecosystems lakes, rivers, streams and other sources of nutrients.

Aspects of the present disclosure also offer distinct technical advantages over existing mass spectrometry technology, including:

demonstrated detection of explosives, chemical warfare agent surrogates, toxic industrial metals and other compounds, volatile organisms from pathogenic bacteria found throughout agriculture plants and products small package (e.g., 1"×1"×2") and can operate for nine hours or more on one charge of helium, which is used as a source of ionization supporting a stable, low powered, pulsed DC discharge. Eluants from the Gas Chromatography (GC) column, flowing counter to the flow of helium from the discharge zone, are ionized by photons from the helium discharge. Bias electrodes focus the resulting electrons toward the collector electrode, where they cause changes in the standing current which are quantified as the detector output is able to achieve sub-parts per billion responses for many chemicals.

The exemplary method of determining chemicals that have a negative effect on colony health uses separation techniques and gas chromatography among other detection techniques to determine the linear dynamic range of target chemical compounds inside honey bee colony. An array of detection devices including any type of carbon/quantum/nano particle, graphene, nanowire, mems, gas chromatography, gas chromatography and/or mass spectrometry (GC/MS), pulsed discharge ionization detector (PDID) or other sensing device in combination with preconcentrators (PC), including micro-PC and Solid-Phase Microextraction (SPME) are used to identify target chemicals.

After target chemicals are identified, more cost-effective nano-sensor are calibrated to detect changes in the level of the target chemicals within a hive and throughout the environment in which social insects interact, specifically agriculture fields. The cost-effective sensors can be doped with various chemicals to improve sensitivity and selectivity as well as withstand high humidity, extreme temperatures and other potential inferences.

One challenge is tracking bee foragers that vanish from the colony. Without such ability, researchers are left to sample and measure diseases, pesticides, and pests from bees that remain in the colony, which is widely considered a non-representative sample. More broadly, studies to date test individual bees, and have not studied bees at the colony-level.

Aspects of the present disclosure deliver advanced sensing technology that will help overcome existing research challenges. Specifically, the high performance portable pheromone and chemical detection system will provide real-time monitoring of the chemical and environmental composition of a colony and how changes in the composition affect pheromone output levels. The resulting time-series data provides researchers the ability to conduct advanced statistical analysis on the chemical composition of colonies and its impact on pheromones and colony formation.

Figure 2:
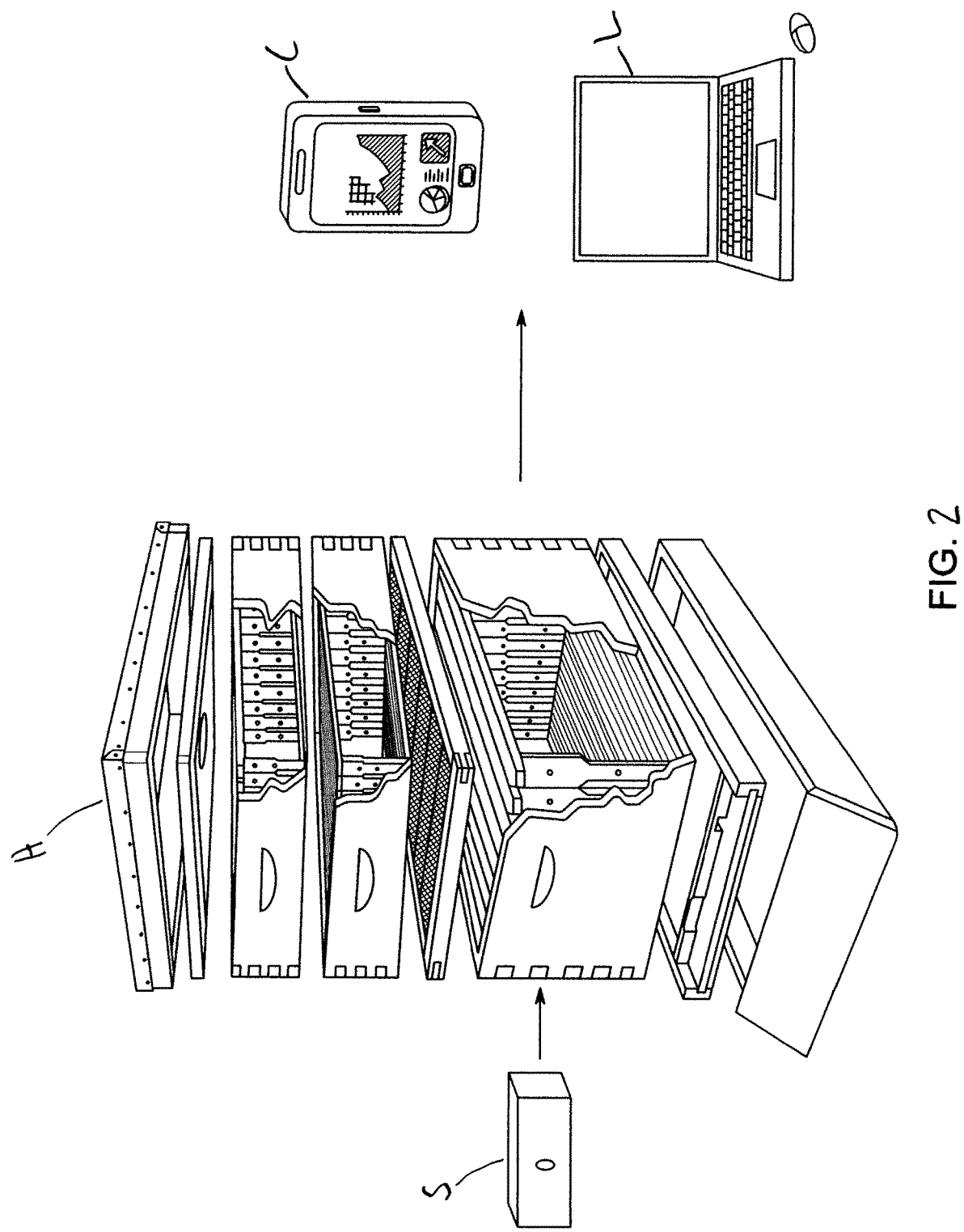
FIG. 2 is a perspective view of a portion of a system in accordance with the present disclosure including a sensor for monitoring an insect environment in the form of a beehive or bee colony.
Figure 3:
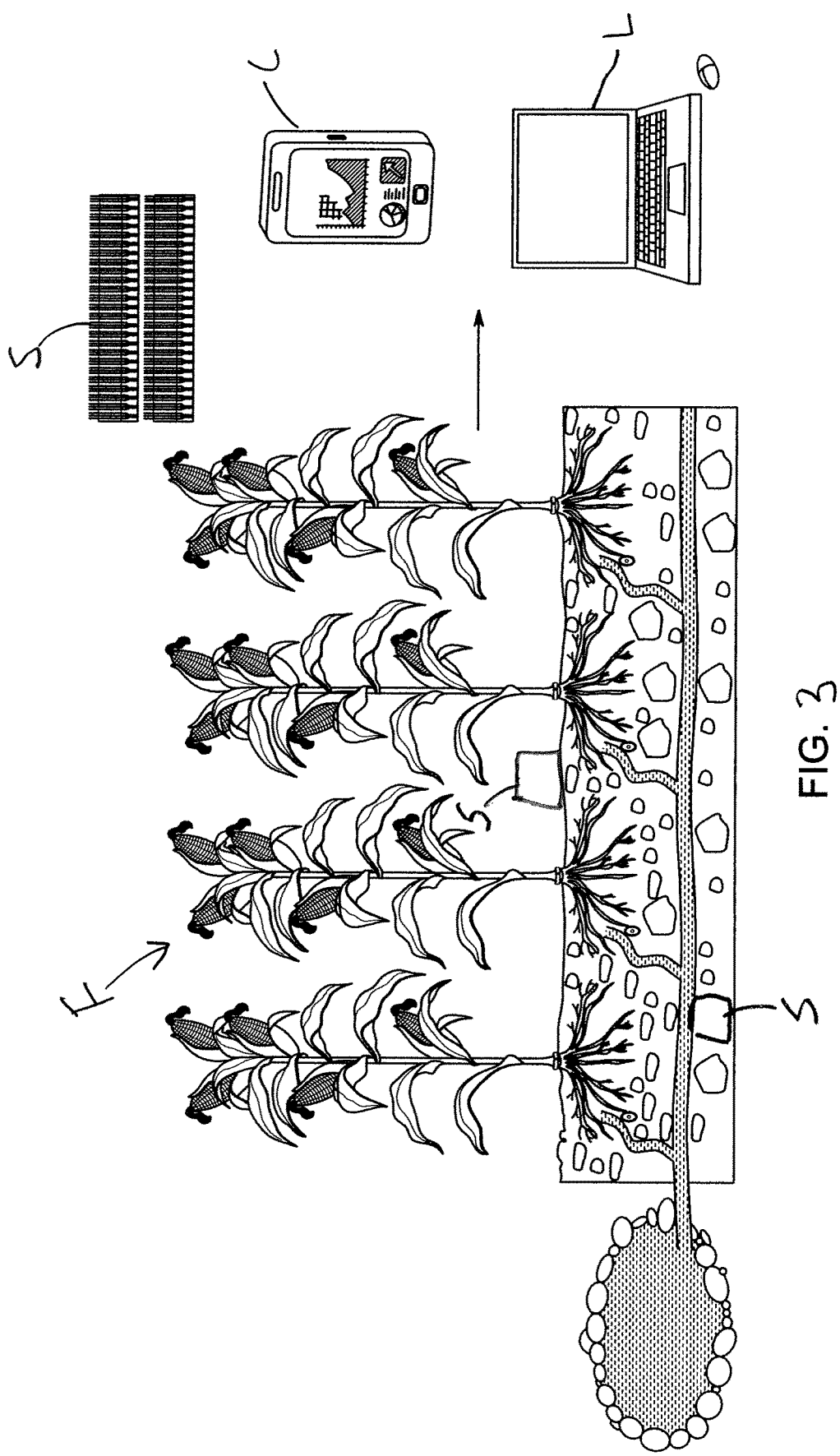
FIG. 3 is a perspective view of a portion of a system in accordance with the present disclosure including a sensor for monitoring an environment external to the beehive in the form of a crop field.

Turning to the FIGURES, and initially FIGS. 1 and 2, FIG. 1 illustrates a first portion of an exemplary system in accordance with the present disclosure in connection with an exemplary insect environment in the form of a hive H including a sensor S. As will be described below, the sensor S can include sensors for detecting chemicals, temperature, humidity, and/or insect activity within the hive H that can be correlated to an insect population. The sensor S is configured to transmit sensed data relating to, among other things, the presence of certain chemicals within the hive H to a receiver. The receiver in the illustrated embodiment can be a cell phone C or other mobile computing device, a laptop L, or any other suitable receiver. In general, the data will be transmitted wirelessly from the sensor S to the one or more receivers, but wired connections are also possible.

With further reference to FIG. 2, an exemplary environment external to the insect environment is illustrated in the form of a crop field F. As will be appreciated, bees from the beehive are expected to interact with the crops in the crop field F to perform pollination of the crops. One or more sensors S are located in the crop field in various locations for sensing, among other things, the presence of one or more chemicals within the crop field F. The sensors S can be in ground sensors or can be above ground sensors. In some applications, a large network of sensors can be deployed throughout the crop field at various locations. The sensors can also be placed on stationary and mobile units including, but not limited to farming equipment and irrigation infrastructure, drones and other remotely piloted or unmanned and autonomous vehicles. In the illustrated example, the sensors S in the hive H and the crop field F are the same. In other embodiments, the sensors S can be different. The sensors S in the crop field F are configured to transmit sensed data to a receiver. Like FIG. 1, the receiver in the illustrated embodiment can be a cell phone C or other mobile computing device, a laptop L, or any other suitable receiver. In general, the data will be transmitted wirelessly from the sensors S to the one or more receivers, but wired connections are also possible. It should be appreciated that the sensors S in the hive H and in the crop field F can be configured to communicate with a common receiver, such that data from all sensors can be analyzed by the receiver or other data processing device.

Figure 4:
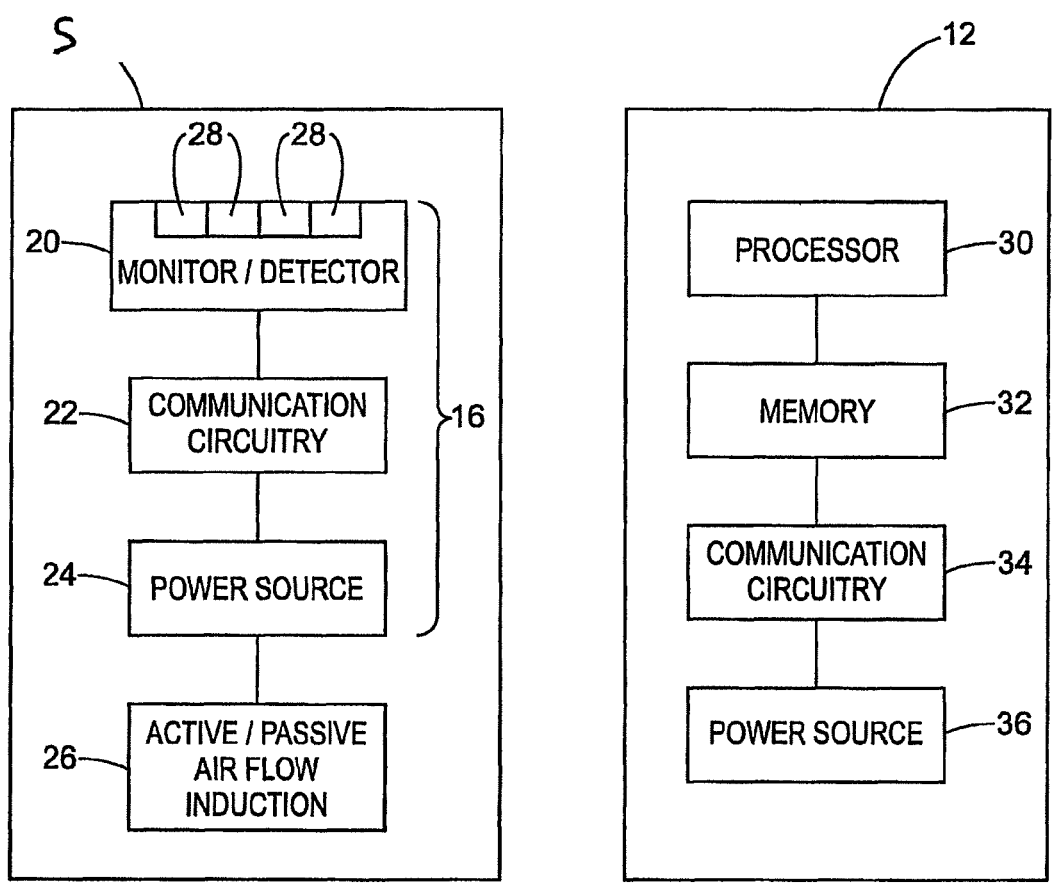
FIG. 4 is a block diagram of an exemplary sensor unit and receiver component in accordance with the present disclosure.

Turning to FIG. 4, each sensor component S includes communication circuitry 22 and a power source 24. The communication circuitry 22, in one embodiment, includes at least one of a near field communication device, Bluetooth communication device, WIFI communication device, or any other suitable communication circuitry for establishing communications with a remote processing device 12. The power source 24 can be a power supply such as a battery (lithium or other including solar cell) mounted or otherwise contained within case 10. In other embodiments, the power source 24 can be an antenna configured to receive energy wirelessly and supply the received energy to one or both of the monitor/detector component 20 and/or communication circuitry 22 such that no onboard battery is required for operation of the monitor system 16.

An active or passive air flow induction device 26 can be provided for ensuring adequate and or continuous flow of air to the monitor/detector component 20. Such devices can include fans, micropumps, louvers, vents etc. An active induction device can be separately replaceable within the system and can include its own power supply. Alternatively, an active induction device can be configured to receive power from power supply 24.

It should be appreciated that the monitor/detector component 20 can comprise a plurality of sensors 28. The sensors 28 can be individually replaceable or can be replaced as a unit. Replacement of the sensors may be necessary due to sensor degradation. In other situations, a user may wish to detect certain chemicals and will choose which sensors to install in the system. In one embodiment, the entire sensor S is replaceable as a unit.

The sensors 28 may detect any environmental factor including temperature or humidity or chemical, such as the chemicals referred to above. The sensors can include thermometers, motion sensors, vibration sensors, acoustic sensors, light sensors, humidity sensors or any other type of sensor as desired.

It will be appreciated that each sensor component S is configured to communicate with the remote processing device 12. That is, each sensor component S collects data and transmits or otherwise shares the collected data with the remote processing device 12 for processing. The remote processing device 12 of the illustrated embodiment includes a processor 30, a memory 32, a communication circuitry 34, and a power source 36. It will be appreciated that the remote processing device 12 can include a wide variety of additional components as is conventional. Such additional components can include a display device, input device, various sensors, various antennas, etc. In some examples, the processor, memory, circuitry and power source can be onboard the sensor components S and can be screen or ink-jet printed components.

Data collected by the monitor/detector component 20 is transmitted via communication circuitry 22 to communication circuitry 34 of the remote processing device 12. Other data, such as sensor state, status, performance data, and the like can also be transmitted to the remote processing device 12. Any suitable manner of transmitting the data from the sensor S to the remote processing device 12 can be employed.

The data collected and transmitted by the sensor components S is then processed by the remote processing device 12 to detect one or more chemicals in accordance with one or more methods set forth in U.S. Pat. No. 8,629,770 to Hummer et al. and U.S. Pat. No. 7,176,793 to Hummer, which are both hereby incorporated herein in their entireties. To this end, suitable software for analyzing the data is stored in memory 32 of the remote processing device 12. Other detection and/or analyzing methods and techniques, including machine learning and artificial intelligence may also be used in conjunction with aspects of the present disclosure.

In one embodiment, the software stored in memory 32 can be in the form of an application, or "app," that is downloaded from an app store or the like. The app can be provided with various "signatures" of chemicals. The signatures can be compared to the data to determine whether the chemical signature was detected by a sensor component S. The app can be configured to be automatically updated with new signatures as the need to detect particular chemicals arise. That is, it is possible to provide new and/or additional chemical signatures for the app to check against the data to detect specific chemicals.

The app can further include features such as adjustable thresholds. For example, for some chemicals that are routinely present in certain amounts and/or not generally considered dangerous or problematic below certain levels, the application can be configured to detect or trigger an alarm when a threshold amount is met or exceeded. For some chemicals which are considered dangerous or problematic in any amount, the thresholds would not generally be adjustable. Among these chemicals are highly toxic metals, plant pathogens, pathogenic bacteria, foodborne pathogen and disease including but not limited to: Norovirus, Toxoplasma Gondii, *Salmonella Typhimurium, Salmonella Enteritidis, Staphylococcus Aureus, Listeria Monocytogenes, Clostridium Perfringens, Vibrio Vulnificus, Yersinia Enterocolitica, Shigella, Cryptosporidium Parvum, Vibrio Parahaemolyticus, Escherichia Coli, Hepatitis, Botulism*, and *Campylobacter Jejuni*.

The app can be further configured to, once a chemical is detected, share the detection information. For example, the application can be configured to use the communication circuitry 34 to broadcast an alert (or generate a notification) via any suitable communications network (e.g., WIFI, NFC, Bluetooth, cell, etc.). The alert may be directly sent to other, for example, personal communication device of a beekeeper, or may be sent to a server (or through a network) and then on to devices within a range of a given location. The alert can also be sent to related stakeholders such as the United States Department of Agriculture (USDA), Food and Drug Administration (FDA) and any other Federal, State or Local authority or organization associated with agriculture production. Furthermore, this real-time data can be used to populate an analytics dashboard of chemical and environmental threats to agriculture production.

As used herein, the terms beehive or hive refers generally to a structure regardless of the presence of bees, whereas the term colony is used when there are bees present in the hive or beehive.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method of monitoring at least one chemical concentration or analyte of an insect environment and a natural ecosystem external to the insect environment comprising:
   monitoring the insect environment for the at least one chemical concentration or analyte using at least one sensor located within the insect environment, the at least one sensor operative to generate data indicative of the at least one chemical concentration or analyte of the insect environment and communicate the data to an associated data processing device;
   monitoring one or more natural ecosystems external to the insect environment with which an insect population of the insect environment interacts with at least one sensor, the at least one sensor operative to generate data indicative of the at least one chemical concentration or analyte and communicate the data to the associated data processing device; and
   taking remedial action to mitigate effects on the insect population based at least in part on the data generated by one or more of the sensors;
   wherein the remedial action includes altering at least one of planting, growing or harvesting conditions, farming methods, processes or procedures;
   wherein the at least one sensor external to the insect environment further determines at least one of a location or operating status of the sensor.

2. The method of claim 1, further comprising monitoring at least one of temperature, humidity, moisture, light, nutrients, vegetation, pH, oxygen, solar radiation, wind speed, vibration, pressure or noise of the insect environment or its natural ecosystem surrounding.

3. The method of claim 1, wherein the insect environment includes a beehive or bee colony and its natural ecosystem includes at least one of a field, vegetation, water source, farming infrastructure or farming equipment.

4. The method of claim 1, wherein at least one of the sensors is configured to periodically report generated data to the associated data processing device over a period of time corresponding to one or more of the presence or absence of at least one chemical, temperature, humidity, moisture, light, nutrient, vegetation, pH, oxygen, solar radiation, wind speed, vibration, pressure or noise.

5. The method of claim 1, further comprising providing a power source including an antenna configured to receive energy wirelessly and supply the received energy to at least one of the sensors.

6. The method of claim 1, wherein at least one of the sensors includes a printed element.

7. The method of claim 1, wherein at least one of the sensors is part of a removable/replaceable component.

8. The method of claim 1, further comprising directing flow of air or liquid or other substance to at least one of the sensors using an active/passive flow induction device.

9. The method of claim 1, further comprising selectively attaching a housing directly to an associated receiver or a protective case of an associated receiver.

10. The method of claim 1, wherein the associated receiver includes a personal communication device.

11. The method of claim 1, wherein the associated receiver includes a non-transitory computer readable medium storing instructions causing the processor to execute an application for processing the data, the application configured to: receive the data or information from the monitoring or measuring device; and analyze the data to detect or interpret one or more chemicals or materials or factors.

12. A monitoring system for monitoring at least one chemical concentration or analyte of an insect environment and a natural ecosystem external to the insect environment comprising:
a receiver;
a first sensor including a detector component operative to generate data corresponding to at least one chemical concentration or analyte, communication circuitry and a power source operatively coupled to the detector component and the communication circuitry for supplying power thereto, the communication circuitry configured to transmit data generated by the detector component to the receiver; and
a second sensor including a detector component operative to generate corresponding to at least one chemical concentration or analyte, communication circuitry and a power source operatively coupled to the detector component and the communication circuitry for supplying power thereto, the communication circuitry configured to transmit data generated by the detector component to the receiver;
wherein the first sensor is configured to detect one or more chemical concentrations or analytes or characteristics in the insect environment;
wherein the second sensor is configured to detect one or more chemical concentrations or analytes or characteristics in an ecosystem external to the insect environment with which the insect population interacts; and
wherein the second sensor is further configured to determine at least one of a location or operating status of the second sensor.

13. The system of claim 12, wherein the monitoring system includes a protective covering made of a breathable material.

14. The system of claim 12, wherein the first or second sensor includes at least one of an electrochemical sensor, microneedle sensor, microelectromechanical system sensor, photoionization detector, gas chromatography sensor, spectroscopy sensor, metal oxide sensor, acoustic sensor, surface acoustic wave sensor, vibration sensor, temperature sensor, humidity sensor, moisture sensor, pH sensor, nutrient sensor, light sensor, infrared sensor, nondispersive infrared sensor, ultrasonic sensor, chemical sensor or an optical sensor.

15. The system of claim 14, wherein the data processing device is configured to generate an alert in response to a detected change in population or activity or health of the insect environment.

16. The system of claim 15, wherein the data processing device is configured to generate an alert in response to detection of a predetermined chemical or chemical concentration or analyte or material or factor in the insect environment.

17. The system of claim 16, wherein the power source of at least one of the first or second sensors includes an antenna configured to receive energy wirelessly and supply the received energy to at least one of the detector component or the communication circuitry.

* * * * *